US00PP25318P3

(12) United States Plant Patent
Kardos et al.

(10) Patent No.: US PP25,318 P3
(45) Date of Patent: Feb. 24, 2015

(54) ***HYPERICUM* PLANT NAMED 'PIIHYP-I'**

(50) Latin Name: ***Hypericum kalmianum* L.**
Varietal Denomination: PIIHYP-I

(71) Applicants: Joshua H. Kardos, Watkinsville, GA (US); Michael A. Dirr, Bogart, GA (US)

(72) Inventors: Joshua H. Kardos, Watkinsville, GA (US); Michael A. Dirr, Bogart, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 133 days.

(21) Appl. No.: 13/815,701

(22) Filed: Mar. 14, 2013

(65) Prior Publication Data

US 2014/0283270 P1 Sep. 18, 2014

(51) Int. Cl.
*A01H 5/00* (2006.01)

(52) U.S. Cl.
USPC ..... Plt./442

(58) Field of Classification Search
USPC ..... Plt./442
See application file for complete search history.

*Primary Examiner* — Susan McCormick Ewoldt
(74) *Attorney, Agent, or Firm* — Lathrop & Gage LLP

(57) ABSTRACT

A new and distinct cultivar of *Hypericum* plant named 'PIIHYP-I', characterized by its compact, mounding growth habit, silver-green foliage, bright yellow flowers from late spring to early summer, and cinnamon brown exfoliating bark.

4 Drawing Sheets

Genus and species of plant claimed: *Hypericum kalmianum* L.

Variety denomination: 'PIIHYP-I'.

BACKGROUND OF THE INVENTION

The present invention relates to a new and distinct cultivar of *Hypericum* plant, botanically known as *Hypericum kalmianum* L., and hereinafter referred to by the cultivar name 'PIIHYP-I'. 'PIIHYP-I' is grown primarily as an ornamental for landscape use and for use as a potted plant.

'PIIHYP-I' originated in 2008 from open-pollinated seed of 'Cfflpc-1' (unpatented) as part of a breeding program in Watkinsville, Ga. 'PIIHYP-I' originated and was selected by the inventor in a cultivated environment in Watkinsville, Ga. from the progeny of this open-pollination by continued evaluation for growth habit and foliage and flower characteristics.

Asexual reproduction of 'PIIHYP-I' by stem cuttings in Watkinsville, Ga. since 2010 has shown that all the unique features of 'PIIHYP-I', as herein described, are stable and reproduced true-to-type through successive generations of such asexual propagation.

SUMMARY OF THE INVENTION

Plants of the new cultivar 'PIIHYP-I' have not been observed under all possible environmental conditions. The phenotype may vary somewhat with changes in light, temperature, soil and rainfall without, however, any variance in genotype.

The following traits have been repeatedly observed and are determined to be unique characteristics of 'PIIHYP-I'. These characteristics in combination distinguish 'PIIHYP-I' as a new and distinct cultivar:

1. Compact, mounding growth habit;
2. Silver-green foliage;
3. Bright yellow flowers from late spring to early summer; and
4. Cinnamon brown exfoliating bark.

Plants of 'PIIHYP-I' differ from plants of the parent, 'Cfflpc-1', primarily in growth habit and stem strength. Plants of 'PIIHYP-I' have a compact, mounding growth habit with strong stems that do not splay with age, whereas plants of 'Cfflpc-1' have an overall larger, rounded growth habit with stems that tend to splay with age, causing the plant to become open in the center.

Plants of the new *Hypericum* 'PIIHYP-I' can be compared to plants of the cultivar 'Deppe' (U.S. Plant Pat. No. 20,045), but differ primarily in foliage color. Plants of 'PIIHYP-I' have silver-green foliage, whereas plants of 'Deppe' have dark green foliage.

BRIEF DESCRIPTION OF THE DRAWINGS

The accompanying color photographs illustrate the flower and foliage characteristics and the overall appearance of 'PIIHYP-I', showing the colors as true as it is reasonably possible to obtain in color reproductions of this type. Colors in the photographs may differ slightly from the color values cited in the detailed botanical description which accurately describe the colors of 'PIIHYP-I'.

DETAILED DESCRIPTION

Figure 1:
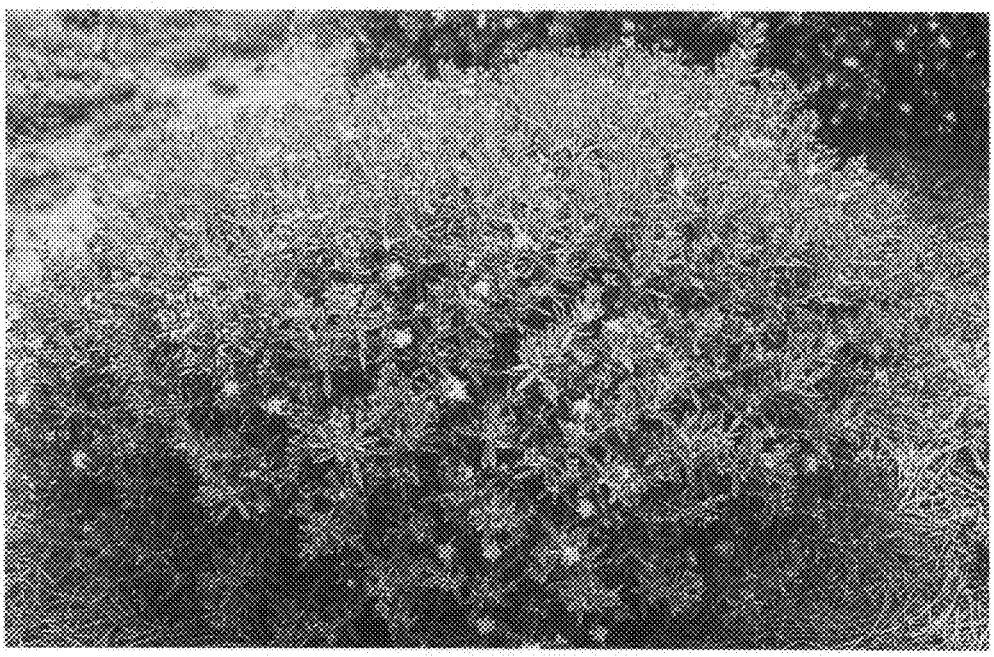
FIG. 1 illustrates the overall appearance and growth habit of a mature plant of 'PIIHYP-I' planted in the ground.
Figure 2:
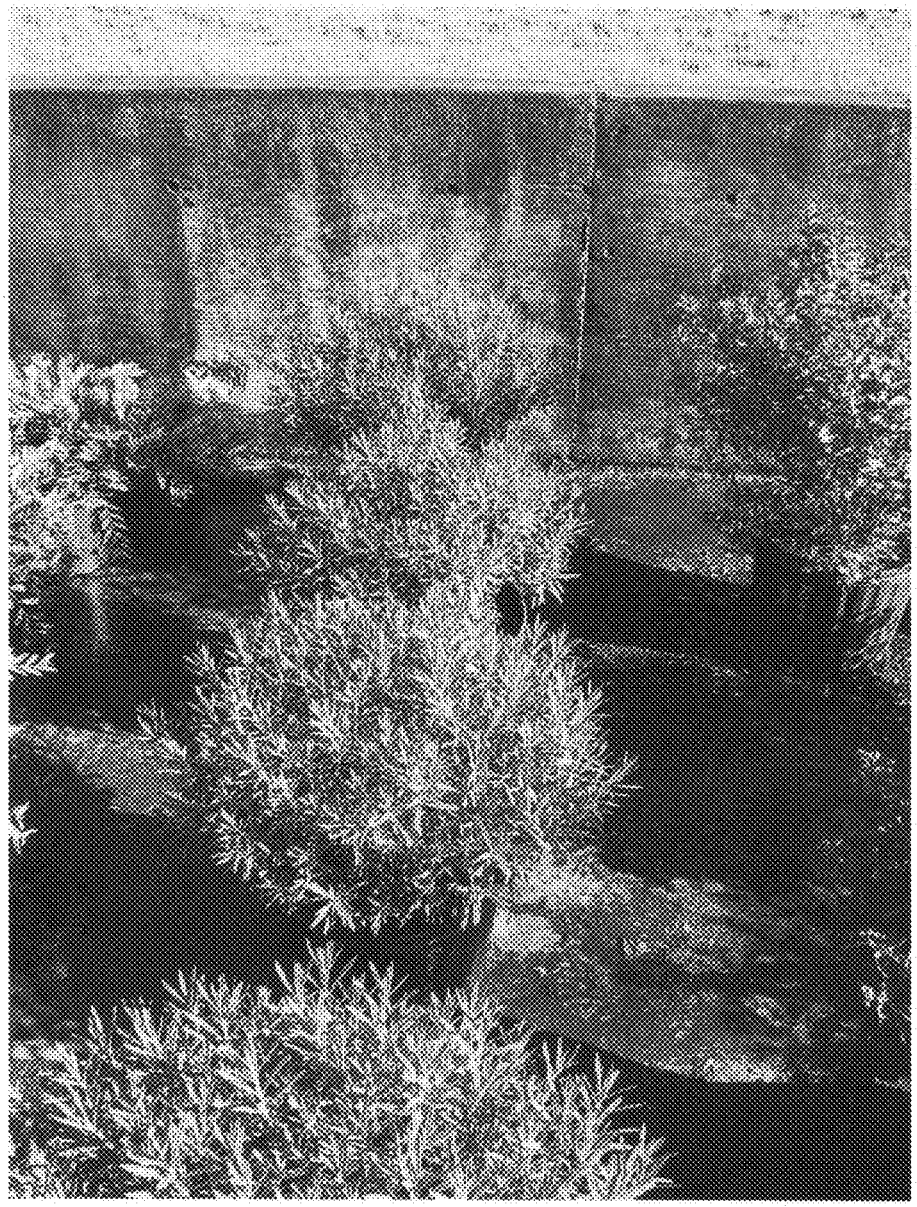
FIG. 2 illustrates the overall appearance of 'PIIHYP-I' plants growing in containers.
Figure 3:
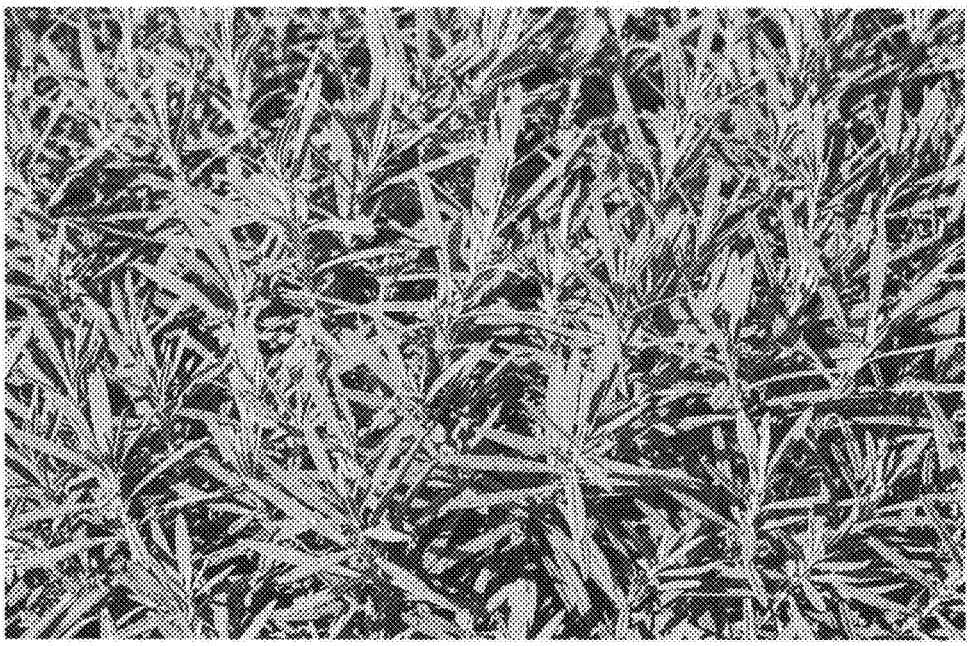
FIG. 3 illustrates a close-up view of the foliage of 'PIIHYP-I'.
Figure 4:
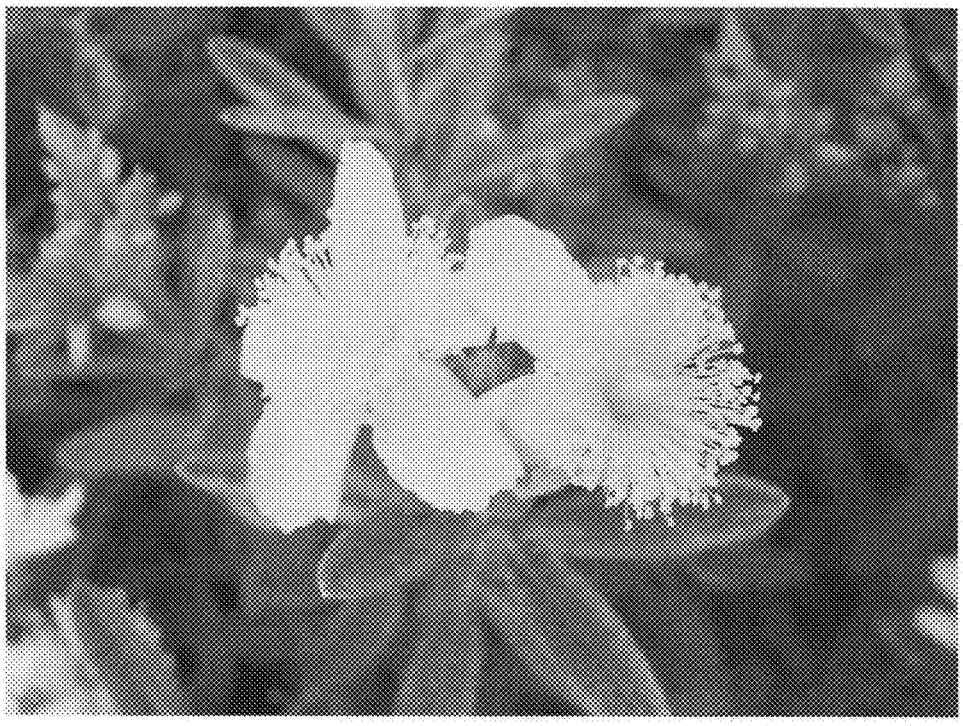
FIG. 4 illustrates a close-up view of the flowers of 'PIIHYP-I'.

In the following description, color references are made to The Royal Horticultural Society Colour Chart, 2007 Edition, except where general terms of ordinary dictionary significance are used. Plants used for the description were approximately 2-years-old and were grown in 11.8 L containers under outdoor conditions in Watkinsville, Ga.

Botanical classification: *Hypericum kalmianum* L., cultivar 'PIIHYP-I'.

Parentage: *Hypericum kalmianum* 'Cfflpc-1' (U.S. Plant Pat. No. 20,045).

Propagation: Stem cuttings.

*Time to initiate roots in summer*.—About 28 days at 32° C.

Plant description: Deciduous flowering shrub; multi-stemmed; compact, mounding growth habit. Freely branching; removal of the terminal bud enhances lateral branch development.

*Root description*.—Fibrous, well-branched.

*Plant size*.—The original plant, now about four and a half-years-old in the ground, is about 61 cm high from the soil level to the top of the inflorescences and about 117 cm wide. First year stems having a diameter of about 1.5 mm. Shape: round. First year stem color: 138C. Second year and older stems have a diameter of about 2 mm or more. Shape: 2-angled. Second year and older stem color: 199C. Bark begins to exfoliate on second year and older stems.

*Stem strength*.—Flexible when young, becoming strong with maturity.

*Internode length*.—About 1.3 cm.

*Trunk diameter*.—About 2.8 cm at the soil line.

*Color*.—200D.

*Bark*.—Exfoliates in papery strips.

Vegetative buds:

*Arrangement*.—Opposite.

*Shape*.—Leaf like, consisting of two to four preformed leaves.

*Size*.—About 1.5 mm in length and about 2 mm in width.

*Color*.—146B.

Foliage:

*Arrangement*.—Opposite, simple.

*Length*.—About 4.7 cm.

*Width*.—About 5 mm.

*Shape*.—Linear to lanceolate.

*Apex*.—Obtuse.

*Base*.—Cuneate.

*Margin*.—Entire.

*Texture* (*upper and lower surfaces*).—Smooth, glaucous.

*Venation pattern*.—Pinnate.

*Venation color of mature foliage* (*upper surface*).—Color is 129A.

*Venation color of mature foliage* (*lower surface*).—132D.

*Color of emerging foliage* (*upper surface*).—124C.

*Color of emerging foliage* (*lower surface*).—128B.

*Color of mature foliage* (*upper surface*).—129A.

*Color of mature foliage* (*lower surface*).—132D.

*Petiole length*.—About 2 mm.

*Petiole diameter*.—About 1.5 mm.

*Petiole color* (*upper and lower surfaces*).—136D.

Flowers:

*Flower type and habit*.—Flowers are borne in multi-branched, terminal cymes.

*Inflorescence*.—About 6 cm in width and about 4 cm in height. Approximately 3 to 9 flowers per inflorescence.

*Natural flowering season*.—Late spring to early summer, approximately May to June in Watkinsville, Ga. Individual flowers are showy for approximately 5 days, are self-cleaning, and are not fragrant.

*Flower buds*.—About 5 mm in width, about 8 mm in length, and 1B in color.

*Flower size*.—About 2.6 cm in diameter and about 1 cm in height.

*Peduncles*.—About 3 cm in length, about 1.5 mm in width, and 138C in color.

*Pedicels*.—About 7 mm in length, about 1 mm in width, and 138C in color.

*Petals*.—5 in a single whorl. Length: about 1.2 cm. Width: about 6 mm. Shape: Oblong. Apex: Obtuse to truncate. Base: Attenuate. Margin: Entire. Color (upper and lower surfaces): 2B. Texture (upper and lower surfaces): Smooth, glabrous.

*Sepals*.—5 in a single whorl. Length: about 5 mm. Width: about 3 mm. Shape: Lanceolate. Apex: Acute. Base: Cuneate. Margin: Entire. Color (upper and lower surfaces): 144C. Texture (upper and lower surfaces): Smooth, glabrous.

Stamens:

*Quantity/arrangement*.—About 220 per flower.

*Filament*.—About 6 mm in length, less than 0.5 mm in width, and 5B in color.

*Anthers*.—About 1.5 mm in length, about 1 mm in width, and 6A in color.

*Pollen*.—Produced in large quantities and is 6A in color.

Pistils:

*Quantity*.—One per flower.

*Size*.—About 6.5 mm in height and about 2.5 mm in width.

*Stigma*.—One per pistil, round in shape, about 0.5 mm in diameter, 149A in color.

*Style*.—1 per pistil, about 2.5 mm in length, and 149A in color.

*Ovary*.—Superior, one per flower, about 2.5 mm in width, about 3.5 mm in height, and 149A in color.

Fruit: The fruit is a dehiscent, 3 or 4-valved capsule, and persists throughout winter.

*Length*.—7 mm.

*Width*.—4 mm.

*Color*.—N199B.

*Seeds*.—Very small, less than 0.5 mm in diameter, many per capsule, and 165A in color.

Disease/pest resistance: Plants of the new *Hypericum* grown in the nursery and garden have not been noted to be resistant to pathogens and pests common to *Hypericum*.

We claim:

1. A new and distinct *Hypericum* plant named 'PIIHYP-I', as illustrated and described herein.

* * * * *